(12) United States Patent
Bei et al.

(10) Patent No.: US 9,107,736 B2
(45) Date of Patent: Aug. 18, 2015

(54) HIGHLY TRACKABLE BALLOON CATHETER SYSTEM AND METHOD FOR COLLAPSING AN EXPANDED MEDICAL DEVICE

(75) Inventors: Nianjiong Joan Bei, Foster City, CA (US); Joanna Lubas, Fremont, CA (US); Ana Montano-Morse, Union City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 2072 days.

(21) Appl. No.: 11/608,448

(22) Filed: Dec. 8, 2006

(65) Prior Publication Data

US 2008/0140051 A1 Jun. 12, 2008

Related U.S. Application Data

(63) Continuation-in-part of application No. 11/567,682, filed on Dec. 6, 2006, now abandoned.

(51) Int. Cl.
*A61M 29/00* (2006.01)
*A61F 2/01* (2006.01)

(52) U.S. Cl.
CPC ......... *A61F 2/013* (2013.01); *A61F 2230/0006* (2013.01)

(58) Field of Classification Search
CPC ......... A61F 2/013; A61F 2/095; A61F 2/958; A61F 2230/0006
USPC ........ 604/93.01, 95.03, 96.01, 523–529, 532, 604/536, 539; 606/108, 191, 192, 194, 198, 606/200; 623/1.11, 1.15, 1.2

See application file for complete search history.

(56) References Cited

U.S. PATENT DOCUMENTS

| | | | |
|---|---|---|---|
| 4,710,181 A | 12/1987 | Fuqua | |
| 5,092,839 A * | 3/1992 | Kipperman | 606/194 |
| 5,246,421 A | 9/1993 | Saab | |
| 5,342,297 A * | 8/1994 | Jang | 604/508 |
| 5,453,090 A | 9/1995 | Martinez et al. | |
| 5,549,551 A * | 8/1996 | Peacock et al. | 604/103.05 |
| 5,562,620 A | 10/1996 | Klein et al. | |
| 6,019,777 A * | 2/2000 | Mackenzie | 606/198 |
| 6,096,009 A | 8/2000 | Windheuser et al. | |
| 6,126,652 A | 10/2000 | McLeod et al. | |
| 6,168,579 B1 * | 1/2001 | Tsugita | 604/96.01 |
| 6,190,393 B1 | 2/2001 | Bevier et al. | |
| 6,264,671 B1 * | 7/2001 | Stack et al. | 606/198 |
| 6,287,291 B1 * | 9/2001 | Bigus et al. | 604/523 |
| 6,309,379 B1 * | 10/2001 | Willard et al. | 600/467 |
| 6,344,045 B1 | 2/2002 | Lim et al. | |
| 6,569,184 B2 | 5/2003 | Huter | |
| 6,613,014 B1 | 9/2003 | Chi | |
| 6,645,223 B2 * | 11/2003 | Boyle et al. | 606/200 |
| 6,663,651 B2 | 12/2003 | Krolik et al. | |
| 6,746,469 B2 * | 6/2004 | Mouw | 606/200 |

(Continued)

FOREIGN PATENT DOCUMENTS

| WO | WO 96/01591 | 1/1996 |
|---|---|---|
| WO | WO 2006/032686 | 3/2006 |

*Primary Examiner* — David Eastwood
(74) *Attorney, Agent, or Firm* — Fulwider Patton LLP

(57) ABSTRACT

A balloon catheter having a pre-mounted recovery sheath for recovering an expanded device, such as an embolic protection device, in a patient's body lumen, and a method of using a balloon catheter system of the invention to recover the expanded device.

22 Claims, 5 Drawing Sheets

(56) References Cited

U.S. PATENT DOCUMENTS

| | | |
|---|---|---|
| 6,884,257 B1 | 4/2005 | Cox |
| 6,887,256 B2 | 5/2005 | Gilson et al. |
| 6,929,652 B1 | 8/2005 | Andrews et al. |
| 7,892,215 B2 * | 2/2011 | Melsheimer et al. ......... 604/284 |
| 2001/0016753 A1 | 8/2001 | Caprio et al. |
| 2002/0058963 A1 | 5/2002 | Vale et al. |
| 2002/0120287 A1 | 8/2002 | Huter |
| 2002/0121472 A1 | 9/2002 | Garner et al. |
| 2002/0161377 A1 * | 10/2002 | Rabkin ......................... 606/108 |
| 2003/0004537 A1 * | 1/2003 | Boyle et al. .................... 606/200 |
| 2003/0114879 A1 | 6/2003 | Euteneuer et al. |
| 2005/0113804 A1 * | 5/2005 | von Lehe et al. .............. 604/528 |
| 2005/0113902 A1 * | 5/2005 | Geiser et al. ................. 623/1.11 |
| 2005/0171473 A1 * | 8/2005 | Gerdts et al. .............. 604/103.04 |
| 2005/0228439 A1 | 10/2005 | Andrews et al. |
| 2006/0129181 A1 | 6/2006 | Callol et al. |
| 2006/0190024 A1 | 8/2006 | Bei et al. |

* cited by examiner

US 9,107,736 B2

HIGHLY TRACKABLE BALLOON CATHETER SYSTEM AND METHOD FOR COLLAPSING AN EXPANDED MEDICAL DEVICE

This application is a continuation-in-part of U.S. application Ser. No. 11/567,682, filed Dec. 6, 2006, the contents of which are incorporated by reference.

BACKGROUND OF THE INVENTION

The present invention relates generally to interventional catheters, and more particularly to a balloon catheter configured for use in an intravascular medical procedure in a stenosed blood vessel.

The treatment of an occluded region of a patient's vasculature commonly includes a percutaneous transluminal interventional procedure such as inflating a catheter balloon and/or implanting a stent inside the blood vessel at the site of the stenosis. For example, in balloon angioplasty, the catheter balloon is positioned across the lesion and inflated with fluid one or more times to a predetermined size at relatively high pressures (e.g. greater than 8 atmospheres) so that the stenosis is compressed against the arterial wall and the wall expanded to clear the passageway. Physicians frequently implant a stent inside the blood vessel at the site of the lesion. Stents may also be used to repair vessels having an intimal flap or dissection or to generally strengthen a weakened section of a vessel. Stents are usually delivered to a desired location within the blood vessel in a contracted condition, and expanded to a larger diameter by release of a radially restraining force (for self-expanding stents) and/or by expansion of the balloon (for balloon expandable stents). The delivery catheter is withdrawn and the expanded stent left implanted within the blood vessel at the site of the dilated lesion.

Such intravascular procedures may release emboli into the circulatory system, which can be extremely dangerous to the patient. Debris that is carried by the bloodstream to distal vessels of the brain may cause these cerebral vessels to occlude, resulting in a stroke, and in some cases, death. Thus, when performed in a carotid artery, an embolic protection device to capture and collect released emboli may be deployed downstream to the interventional catheter. For example, embolic protection devices in the form of filters or traps can be delivered in a collapsed configuration to a location adjacent to the interventional procedure site, radially expanded to open the mouth of the filter or trap, and after the interventional procedure has been performed, the device is collapsed for removal with the captured embolic material therein.

An essential step in effectively performing an interventional procedure is properly positioning the catheter system at a desired location within the patient's vasculature. The catheter shaft must be able to transmit force along the length of the catheter shaft to allow it to be pushed through the vasculature. However, the catheter shaft must also retain sufficient flexibility and low profile to allow it to track over a guidewire through the often tortuous, narrow vasculature. Such deliverability issues must be balanced against one another and against other performance characteristics. As a result, one design challenge has been making the procedure, including the delivery and retrieval of the components of the catheter system, as quick and easy as possible.

SUMMARY OF THE INVENTION

The invention is directed to a balloon catheter having a pre-mounted recovery sheath for recovering an expanded device, such as an embolic protection device, in a patient's body lumen. Another aspect of the invention is a method of using a balloon catheter system of the invention to recover the expanded device.

A balloon catheter system of the invention generally comprises a balloon catheter having a proximal end, a distal end, an elongated shaft with an inflation lumen, and a balloon on a distal shaft section with an interior in fluid communication with the inflation lumen, and a recovery sheath having a lumen with the balloon catheter elongated shaft slidably disposed therein. The recovery sheath has a proximal end, a distal end, a retracted configuration in which the distal end is located proximal to the balloon, and an advanced configuration in which the distal end is located distal to the balloon catheter, and has a distal recovery section configured to recover an embolic protection device or other expandable device (i.e., a device which reversibly radially expands and collapses). Following inflation of the balloon to perform a procedure at a treatment site in the body lumen, the recovery sheath is configured to be advanced distally over the deflated balloon, so that an expanded device deployed distal to the treatment site collapses within the distal end of the advanced recovery sheath for repositioning or removal from the body lumen.

In a presently preferred embodiment, the recovery sheath has a transverse cross sectional profile which decreases from a large profile distal recovery section to smaller profile distal shaft section, and which increases from the distal shaft section to a larger profile midshaft section, and which decreases from the midshaft section to a smaller profile proximal shaft section. Typically, the balloon catheter is a rapid exchange-type catheter having a proximal shaft section and a distal shaft section with the device lumen extending in the distal shaft section to a proximal port spaced distally from the proximal end of the elongated catheter shaft, and the variable profile sheath is configured to closely conform to the underlying balloon catheter shaft. As a result, the extent to which the sheath increases the stiffness and profile of the balloon catheter is minimized, thus providing a corresponding improvement in the ability to track the balloon catheter with the sheath mounted thereon on a guidewire or other device.

The recovery sheath has at least a section with a tubular body such that the increasing and decreasing profile of the sheath forms internal shoulders therein (i.e., at the location of a change in the diameter of the sheath lumen). In a presently preferred embodiment, the internal shoulders of the sheath are configured to act as a stop, thereby limiting the longitudinal advancement or retraction of the sheath therealong by contacting underlying portions of the balloon catheter.

In one embodiment, the sheath has a section having an open-walled configuration, preferably with a C-shaped inner surface, which defines a channel and which is configured to extend only partially around the circumference of the elongated shaft of the balloon catheter. Such an open-walled section extending along a proximal portion of the sheath facilitates providing the sheath on a rapid-exchange type balloon catheter. Additionally, the open-walled section further improves trackability of the system by minimizing the profile and stiffness increases resulting from the sheath on the balloon catheter.

In one embodiment, the distal recovery section of the recovery sheath has at least a portion with a corrugated wall which unfolds from a radially collapsed configuration to a radially enlarged configuration. The corrugated distal recovery portion is preferably configured to unfold and thereby radially expand upon application of a radially expansive force against an inner surface of the distal recovery portion in the collapsed configuration. In a presently preferred embodiment, the corrugated wall self-collapses to a radially re-collapsed configuration from the radially enlarged configuration upon the removal of the radially expansive force. As a result, the corrugated tip of the recovery sheath provides a very low profile distal leading end which facilitates advancing the catheter system within the patient's anatomy, while also providing the sheath with an inner lumen which is sized to effectively collapse the expanded device, e.g., embolic protection device.

The recovery sheath has an inner diameter along at least a portion of the distal recovery section of the sheath which is sufficiently large to facilitate sliding the sheath along an expanded operative distal end of the expanded device in order to collapse the operative distal end, e.g., the expanded filter of an embolic protection device. The larger diameter distal recovery section of the sheath reduces the force required to slidably advance the sheath during collapse of an embolic protection device therein (i.e., relative to the smaller diameter shaft section of the sheath located proximal to the larger diameter distal recovery section of the sheath), such that the relatively low detach force of common embolic protection devices is not exceeded. For example, in one embodiment the expandable device (e.g., embolic protection device) has an elongated body which has an expanding frame secured to a distal section thereof with a detach force of less than 1 pound, and the recovery section of the sheath has an inner diameter configured to be slidably advanceable over the frame, to collapse the frame, with a force which does not exceed the detach force of the frame.

A method of using a balloon catheter system to perform a medical procedure and recover an expanded device in a patient's body lumen generally comprises introducing within a patient's body lumen a balloon catheter system having a balloon catheter within a lumen of a recovery sheath, the balloon catheter having a proximal end, a distal end, an elongated shaft with an inflation lumen, and a balloon on a distal shaft section with an interior in fluid communication with the inflation lumen, wherein the recovery sheath is a tube which has the balloon catheter elongated shaft slidably disposed therein, and which has a proximal end, a distal end, a retracted configuration in which the distal end is located proximal to the balloon, and an advanced configuration in which the distal end is located distal to the balloon catheter shaft. The recovery sheath preferably has a transverse cross sectional profile which decreases from a large profile distal recovery section to smaller profile distal shaft section, and which increases from the distal shaft section to a larger profile midshaft section, and which decreases from the midshaft section to a smaller profile proximal shaft section. In the method of the invention, the balloon catheter system is slidably advanced within the patient's body lumen to a desired location adjacent to a deployed expandable device (the expandable device has an operative distal end configured to reversibly radially expand and collapse, was previously delivered and deployed in the body lumen). Typically, the balloon catheter has a device lumen configured to slidably receive a proximal section of the expandable device, so that the balloon catheter is slidably advanced thereover to position the balloon at the desired treatment location proximal to the radially expanded operative distal end of the expandable device. With the balloon catheter in position in the body lumen, the balloon is inflated to perform a medical procedure, and then deflated, and the method includes advancing the recovery sheath over the balloon, and advancing the recovery sheath and balloon catheter together distally to position the operative distal end of the expandable device within the recovery section of the recovery sheath and thereby radially collapse the operative distal end of the expandable device. The balloon catheter with the collapsed operative distal end therein can then be slidably displaced together in the patient's body lumen, to reposition or remove the expandable device from the patient's body lumen.

A balloon catheter system of the invention provides excellent flexibility and low profile due to the profile changes along the length thereof. The system is therefore highly trackable, yet avoids the need to withdraw the balloon catheter from the treatment site before an expanded device, e.g., embolic protection filter, can be recovered within a recovery catheter. As a result, the system provides for ease of use, and minimizes the procedure time. These and other advantages of the invention will become more apparent from the following detailed description and accompanying exemplary drawings.

BRIEF DESCRIPTION OF THE DRAWINGS

FIG. 9 illustrates the balloon catheter system of FIG. 8 with the balloon inflated to radially expand a stent.

FIG. 10 illustrates the balloon catheter system of FIG. 9 with the balloon deflated and the recovery sheath advanced distally over the deflated balloon.

FIG. 11 illustrates the balloon catheter system of FIG. 10 with the embolic protection device radially collapsed in the recovery sheath.

DETAILED DESCRIPTION OF THE PREFERRED EMBODIMENTS

Figure 1:
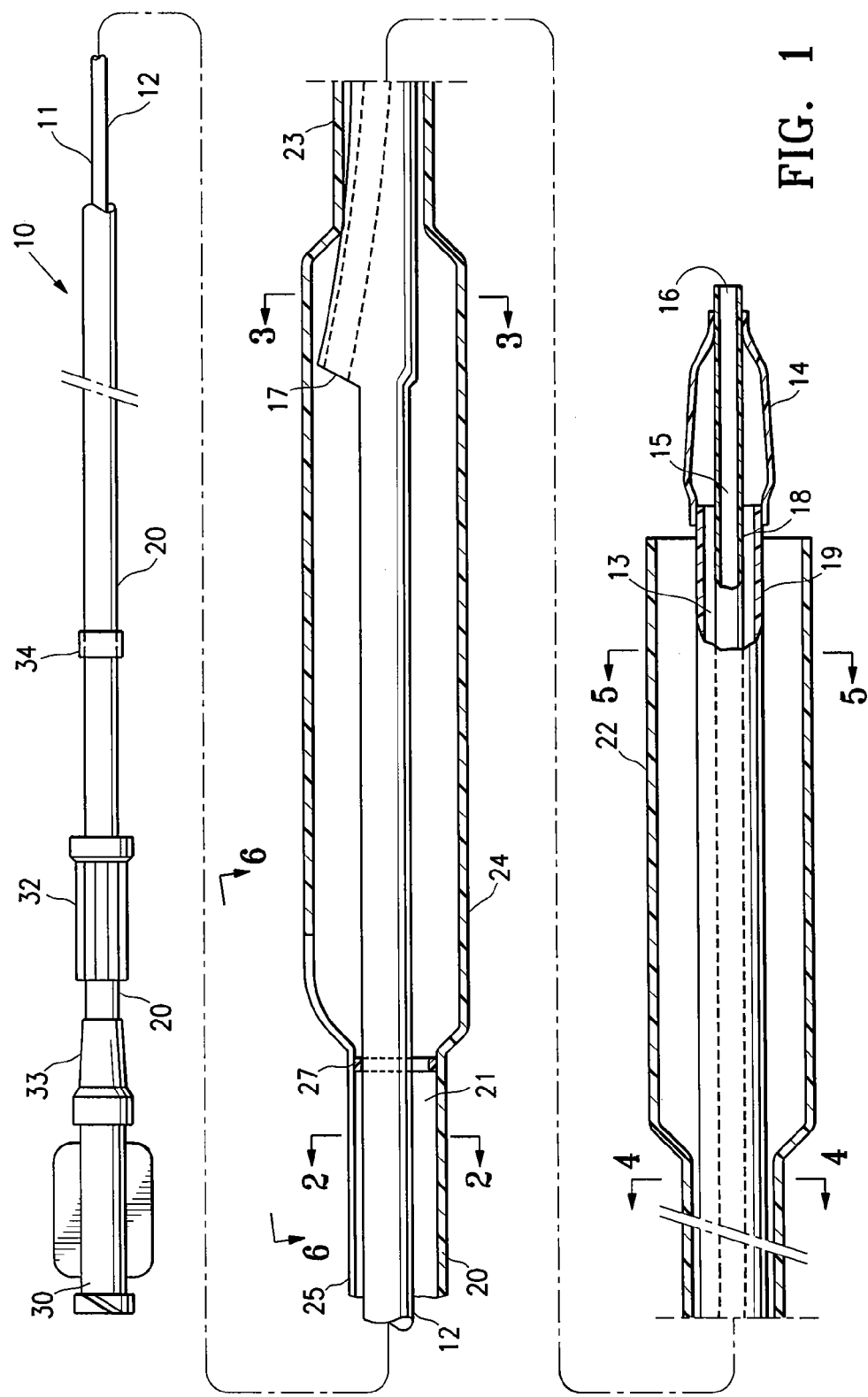
FIG. 1 is an elevational, partially in section, view of a balloon catheter system embodying features of the invention having a recovery sheath pre-mounted on a balloon catheter, with the recovery sheath in a retracted configuration.
Figure 5:
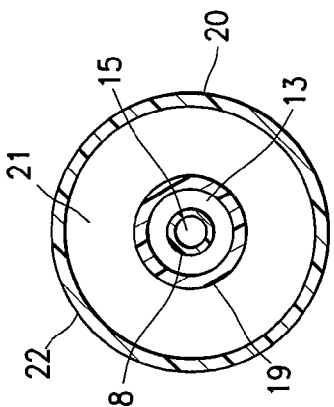
FIGS. 2-5 are transverse cross sections of the catheter of FIG. 1, taken along lines 2-2, 3-3, 4-4, and 5-5, respectively.
Figure 4:
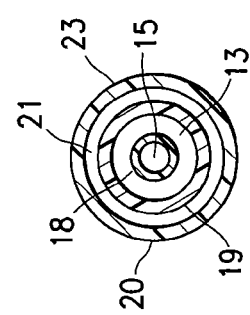
Figure 3:
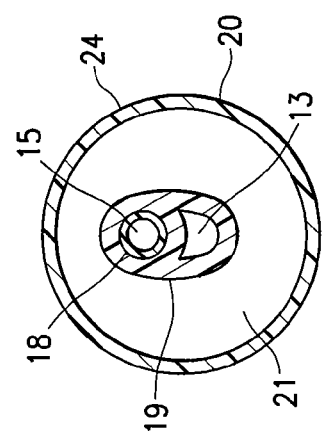
Figure 2:
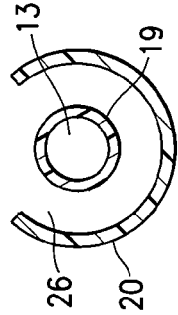
Figure 8:
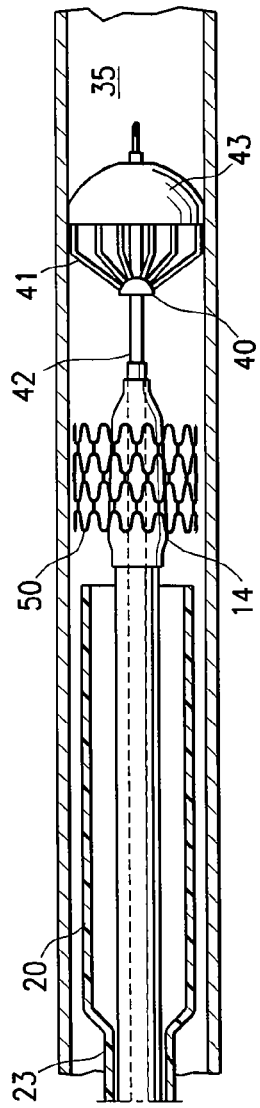
FIGS. 8-11 illustrate the balloon catheter system of FIG. 1 in a method of performing a medical procedure in accordance with an embodiment of the invention, with FIG. 8 illustrating the balloon catheter noninflated balloon positioned at a treatment site in a patient's body lumen and proximal to a deployed embolic protection device.

FIG. 1 illustrates an elevational, partially in section, view of a balloon catheter system 10 embodying features of the invention, generally comprising a balloon catheter 11 having elongated catheter shaft 12 with an inflatable balloon 14 secured to a distal shaft section, and a recovery sheath 20 on the elongated catheter shaft 12 configured to slidably receive at least a portion of an expandable section of an expandable device such as an embolic protection device 40 (see FIG. 8).

The inflatable balloon 14 has an interior in fluid communication with an inflation lumen 13 extending within the shaft 12, so that the balloon inflates from a noninflated configuration to an inflated configuration upon the introduction of inflation fluid to the balloon interior, and deflates to a deflated configuration upon the withdrawal of the inflation fluid. FIG. 1 illustrates the balloon 14 in the low profile noninflated configuration for introduction and advancement within the patient's body lumen prior to inflation of the balloon 14. An adapter 30 secured to the proximal end of the catheter shaft 12 is configured for connecting to an inflation fluid source (not shown) for inflating the balloon 14.

A device lumen 15 in the balloon catheter shaft 12 is configured to slidably receive a guidewire or other wire-type device such as the proximal section of the embolic protection device 40 (see FIG. 8). In the illustrated embodiment, the balloon catheter 11 is a rapid-exchange catheter with a relatively short device lumen 15 extending from a distal port 16 at the distal end of the balloon catheter shaft 12 to a proximal port 17. Proximal port 17 is at a location, typically referred to as the rapid exchange notch, spaced distally from the proximal end of the catheter, such that a proximal shaft section of the balloon catheter shaft 12 has only the inflation lumen 13 therein and not the device lumen 15. In the embodiment of FIG. 1, the balloon catheter shaft 12 comprises an inner tubular member 18 with the device lumen 15 therein, and an outer tubular member 19 with the inflation lumen 13 therein. The balloon 14 has a proximal end sealing secured to the shaft outer tubular member 19 and a distal end sealingly secured to the shaft inner tubular member 18, such that the inflation lumen defined by the annular space between the inner and outer tubular members 18, 19 of the catheter shaft 12 is in fluid communication with the balloon interior. The balloon catheter 11 is illustrated partially in section in FIG. 1, with a proximal section of the inner tubular member 18 shown in dashed lines within the outer tubular member 19. However, a variety of suitable balloon catheter shaft configurations can alternatively be used as are conventionally known, including dual lumen catheter shafts with side-by-side lumens. The inner and outer tubular members 18, 19 of the catheter shaft 12 are illustrated as single layered tubes for ease of illustration, however, it should be understood they can comprise a series of multi-layered or multi-sectioned tubes. For example, the outer tubular member 19 typically comprises a series longitudinally joined members including a distal outer member having a proximal end sealingly secured to the distal end of a midshaft or proximal outer member, and with the proximal shaft section of the balloon catheter shaft 12 typically formed at least in part by a high strength tubular member.

The recovery sheath 20 has a single lumen 21 with the balloon catheter elongated shaft 12 slidably disposed therein. The recovery sheath 20 has a retracted configuration in which the distal end of the sheath 20 is located proximal to the balloon, and an advanced configuration in which the distal end of the sheath is located distal to the distal end of the balloon catheter 11 (i.e., distal to the distal-most end of the balloon catheter shaft 12 at distal port 16). In a presently preferred embodiment, the recovery sheath 20 has a length less than the balloon catheter shaft 12 such in a fully retracted configuration the proximal end of the recovery sheath 20 is distal to the proximal end of the balloon catheter shaft 12. FIG. 1 illustrates the recovery sheath 20 in the fully retracted configuration.

A releasable lock mechanism 32 configured to releasably lock the recovery sheath 20 to the elongated shaft 12 is mounted at strain relief tubing 33 on a proximal end section of the recovery sheath 20. Although illustrated as a simplified structure at the proximal end of recovery sheath 20 for clarity and ease of illustration, typically a more elaborate handle would be provided on the proximal end of the catheter system which has a mechanism which can be activated to move the recovery sheath 20 relative to the catheter shaft 12 therein, and which can have a lock to releasably secure the recovery sheath 20 to the catheter shaft 12. Such handle mechanisms are generally known and typically include a thumb wheel, trigger, lever or other activation mechanism for advancing and/or retracting a shaft. A variety of suitable mechanisms may be used to clamp or otherwise releasably lock the recovery sheath 20 to the elongated shaft 12 as are conventionally known, typically in the form of a clamp or other locking mechanism at or near the proximal end of the recovery sheath 20. A proximal end section of the shaft 12 is received within the strain relief 33 and secured thereto.

In the embodiment illustrated in FIG. 1, the profile of the recovery sheath 20 varies along the length of the sheath 20. Specifically, the recovery sheath 20 has a distal recovery section 22 with a first transverse dimension, a distal shaft section 23 with a second transverse dimension smaller than the first, a midshaft section 24 with a third transverse dimension larger than the second, and a proximal shaft section 25 with a fourth transverse dimension smaller than the third.

Figure 6:
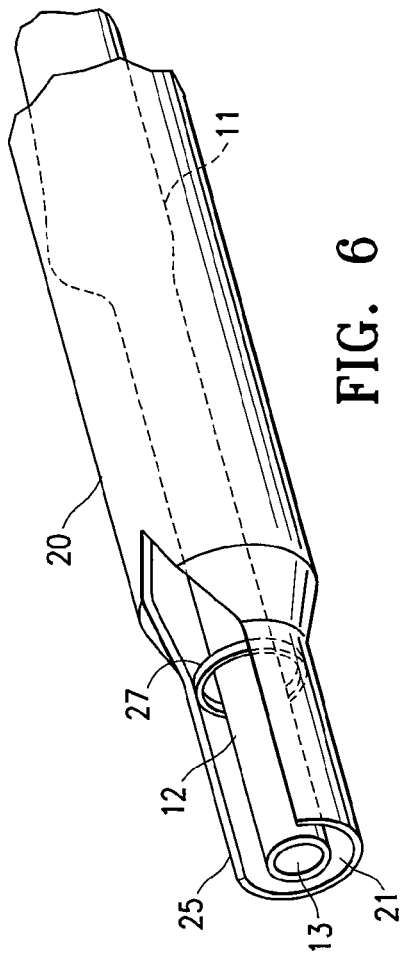
FIG. 6 is a perspective view of a portion of the balloon catheter system of FIG. 1, taken along line 6-6.

FIGS. 2-5 illustrate transverse cross sectional views of the system of FIG. 1, taken along lines 2-2, 3-3, 4-4 and 5-5, respectively. For ease of illustration, the radial distance between the adjacent component parts of the catheter system may be somewhat exaggerated in FIGS. 2-5. As best shown in FIGS. 2-5, the recovery sheath 20 has a tubular body portion along the distal recovery, distal shaft, and midshaft sections 22, 23, 24, respectively, which extends fully around the circumference of the elongated shaft 12 therein. In contrast, the proximal shaft section 25 of the embodiment of sheath 20 shown in FIG. 1 is open-walled with a C-shaped inner surface which defines a channel 26 and which is configured to extend only partially around the circumference of the elongated shaft 12. FIG. 6 illustrates a perspective view of the sheath 20, at the transition from the open-walled proximal section 25 to the midshaft tubular section 24, taken along line 6-6 in FIG. 1, with the balloon catheter 11 shown in dashed lines within the sheath 20.

The entire length of the proximal shaft section 25 of the sheath 20 preferably has the open-walled C-shaped configuration (i.e., from the proximal end of the sheath 20 to the proximal end of the midshaft section 24 of sheath 20). The sheath 20 having the open-walled proximal section 25 and tubular body portion distal thereto is typically made by extruding or otherwise forming a tube and removing a portion of the tube wall along the proximal section to form the open-walled section 25. For example, the tubular polymeric wall can be cut away using a laser or a blade, with about 20% to about 50% (of the circumference) of the wall being removed. The resulting longitudinally extending opening in the wall of the sheath 20, when aligned with the device lumen proximal port 17, effectively forms a port which allows the proximal section of the embolic protection device 40 to emerge from the system 10 at the location of the rapid-exchange proximal port 17. Preferably, the opening in the wall of the sheath proximal section 25 is wider than a section of the balloon catheter shaft 12 extending in the sheath proximal section 25 (see FIG. 2). A collar 34 on the sheath proximal section 25 keeps the balloon catheter shaft 12 within the open-walled proximal section 25, and constrains the rotation thereof to maintain the proximal port 17 aligned with the opening in the wall of the sheath proximal section 25. The collar 34 typically comprises an annular member moveably disposed on the sheath to allow the sheath 20 to be slidably advanced distally while the collar 34 is held substantially stationary. Although the collar 34 is illustrated as being distal to the simplified gripping and locking mechanism 32 of the sheath 20 illustrated in FIG. 1, it should be understood that the collar 34 could be located proximal thereto. However, the collar 34 is typically located distal to the gripping and locking mechanism of the sheath 20, particularly when a more elaborate handle mechanism is provided to move and lock the recovery sheath 20 relative to the catheter shaft 12, as discussed above. The collar 34 is typically located several centimeters distally from the in/deflation port of proximal adapter 30.

Figure 7:
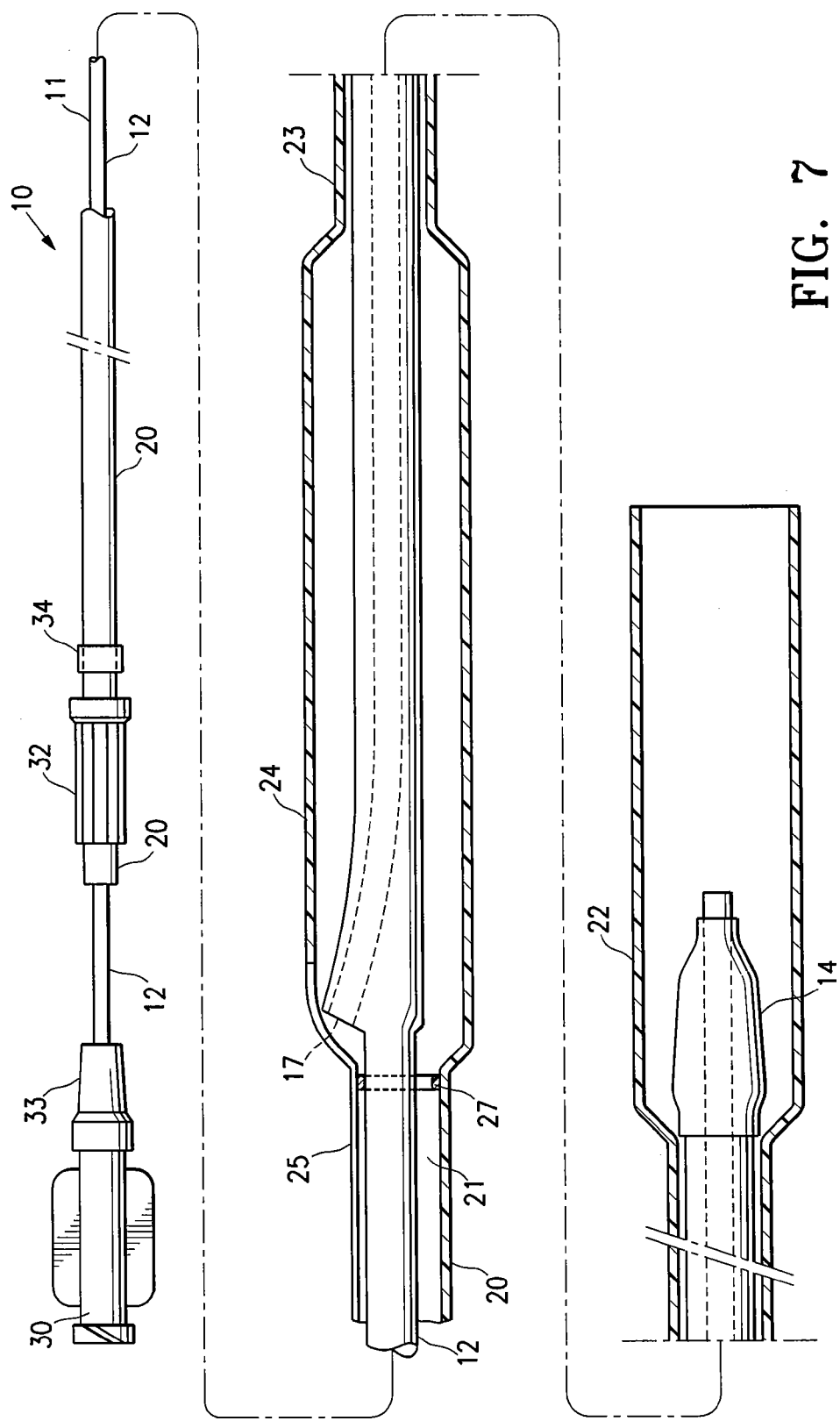
FIG. 7 illustrates the balloon catheter system of FIG. 1 with the recovery sheath in an advanced configuration.

FIG. 7 illustrates the recovery sheath 20 in the advanced configuration, such that the distal end of the recovery sheath 20 is positioned distal to the distal end of the balloon catheter 11 therein. The proximal end of the recovery sheath 20 is shown proximal to the simplified gripping and locking mechanism 32, so that the distally advanced position of the sheath 20 in the advanced configuration of FIG. 7 is clearly illustrated in relation to the retracted configuration of FIG. 1. However, it should be understood that the displacement of the proximal end of the sheath 20 may take place in whole or in part within a more elaborate handle mechanism as discussed above. A stopper 27 at the distal end of the open-walled proximal section 25 is configured to abut the rapid-exchange notch section of the balloon catheter shaft 12 to limit the distal advancement of the sheath 20 over the balloon catheter shaft 12.

Maximizing the length of the C-shaped open proximal section 25 increases the flexibility of the system 10. However, the length of the C-shaped open proximal section 25 is typically selected to also provide a sufficient level of support, in addition to flexibility. In the illustrated embodiment, the C-shaped open proximal section 25 extends along substantially the entire length of the proximal section of the balloon catheter 11, and the distal end of the C-shaped open proximal section 25 of the recovery sheath 20 is proximal to the proximal port 17 of the balloon catheter 11 in both the advanced and retracted configurations. Specifically, in the illustrated embodiment, the distal end of the C-shaped open proximal section 25 is proximally spaced a relatively short distance from the proximal port 17 in the retracted configuration of FIG. 1, and is at (proximally adjacent to) the proximal port 17 in the advanced configuration of FIG. 7. As a result, the midshaft section 24 of the sheath 20 extends across the device lumen proximal port 17 in the retracted and advanced configurations (i.e., the midshaft section 24 has a length sufficiently long such that the proximal end of the midshaft section is proximal to the balloon catheter proximal port 17 and the distal end of the midshaft section is distal to the balloon catheter proximal port 17). However, the C-shaped open proximal section 25 of sheath 20 can have a longer or shorter length than in the illustrated embodiment. For example, in one embodiment (not shown), the sheath 20 has a C-shaped open walled proximal section which extends to a location distal to the proximal port 17 of the elongated catheter shaft 12, at least in the advanced configuration. Therefore, in alternative embodiments (not shown), the midshaft section 24 of the sheath 20 does not necessarily extend across the device lumen proximal port 17 of the balloon catheter 11 in the advanced and/or retracted configurations.

The recovery sheath 20 has internal shoulders formed by the increasing or decreasing inner diameter of the sheath 20 along the length thereof. The internal shoulders preferably act as stops, limiting the advancement and/or retraction of the recovery sheath 20 on the balloon catheter 11 therein. For example, at the distal end of the midshaft section 24, the transition to the smaller diameter distal shaft section 23 of the sheath 20 forms an internal shoulder which contacts a location on the balloon catheter 11 adjacent to the proximal port 17 and thereby limits the retraction of the sheath 20 (see FIG. 1). Similarly, at the proximal end of the distal recovery section 22 of the sheath 20, the transition to the smaller diameter distal shaft section 23 of the sheath 20 forms an internal shoulder which contacts a location on the balloon catheter at the distal end of the deflated balloon and thereby limits further advancement of the sheath 20 in the advanced configuration (see FIG. 7). Although for ease of illustration the various internal shoulders and stops of the sheath 20 may be illustrated slightly spaced apart from the outer surface of the balloon catheter 11 therein, it should be understood that to act as stops they will contact an underlying section of the balloon catheter 11 therein at the limit of advancement or retraction of the sheath 20.

In the illustrated embodiment, the internal shoulders are formed by short, tapered transitions in the inner and outer diameter of the sheath 20. However, one or more of the internal shoulders can be formed by a more gradual, long tapered transition, or by a more abrupt, step-change transition in alternative embodiments (not shown).

FIGS. 8-11 illustrate the balloon catheter system 10 of FIG. 1 during a method of performing a procedure in accordance with an embodiment of the invention, in which the balloon catheter 11 is inflated to perform a medical procedure within a patient's body lumen 35 and then the recovery sheath 20 premounted thereon is used to recover a radially expanded embolic protection device 40 previously deployed in the body lumen 35. Specifically, as illustrated in FIG. 8, the balloon catheter system 10 is advanced within the body lumen 35 to position the noninflated balloon 14 at a treatment site in the body lumen 35 and proximal to the distal end of the deployed embolic protection device 40. The illustrated embolic protection device 40 is of the type having a self-expanding frame 41 which is on a distal section of an elongated core wire 42 and which has a filter 43, and FIG. 8 illustrates the device 40 with the frame 41 radially expanded into contact with the vessel wall inner surface such that the filter 43 will trap embolic material in the body lumen 35. Typically, the embolic protection device is delivered and deployed in the body lumen 35 using a delivery catheter (not shown) which is then removed prior to positioning of the balloon catheter system 10. Details regarding embolic protection devices and delivery systems can be found in U.S. Pat. No. 6,695,813 incorporated by reference herein in its entirety.

In the embodiment illustrated in FIG. 8, the balloon 14 is positioned within a stent 50 which requires a stent touch-up (post-dilation) procedure, commonly performed on self-expanding stents in order to radially expand the stent against the inner surface of the vessel wall to a fully expanded configuration. Thus, the stent 50 has been previously delivered and deployed within the body lumen 30 using a stent delivery catheter (not shown) which is then removed prior to positioning of the balloon catheter system 10, leaving the stent at least partially radially expanded in the body lumen. Details regarding self-expanding stents and delivery systems can be found in U.S. Pat. Nos. 6,695,862 and 6,582,460 incorporated by reference herein in their entireties. Following removal of the stent delivery catheter, the balloon catheter system 10 of the invention is introduced into the body lumen and slidably advanced to the treatment site over the previously deployed embolic protection device 40. Specifically, the device lumen 15 of the balloon catheter shaft inner tubular member 18 is configured to slidably receive and track over the core wire 42 of the embolic protection device 40.

Preferably, the system 10 is introduced and advanced within the body lumen 35 with the recovery sheath 20 locked to the balloon catheter shaft 12 in the fully retracted configuration. To prepare the system for maneuvering to the treatment site within the patient's body lumen, the operator holds the collar 34 and slides the recovery sheath 20 proximally until it stops such that the balloon 14 is exposed, and then locks the recovery sheath 20 to the balloon catheter shaft 12 using the locking mechanism 32.

Figure 9:
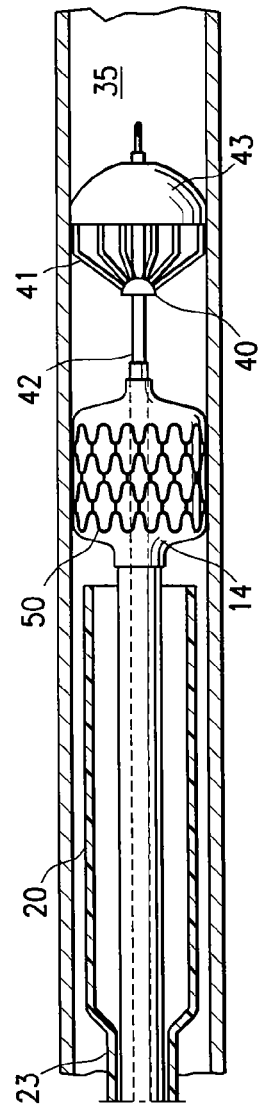

At the treatment site, the balloon 14 is inflated in the body lumen 35 to perform a medical procedure, which in the illustrated embodiment is a post-dilation of the self-expanded stent 50. FIG. 9 illustrates the balloon 16 inflated within the stent 50 in order to radially expand the stent 50 to a fully expanded configuration to thereby implant the stent in the body lumen 35, with the embolic protection device remaining deployed distal to the stent to capture any embolic material released during the procedure. The balloon 14, configured for radially expanding stent 50, typically has a relatively high working pressure (for example, a nominal pressure of about 6 to about 12 atm), and a relatively high wall strength, to expand the stent without rupturing.

Figure 10:
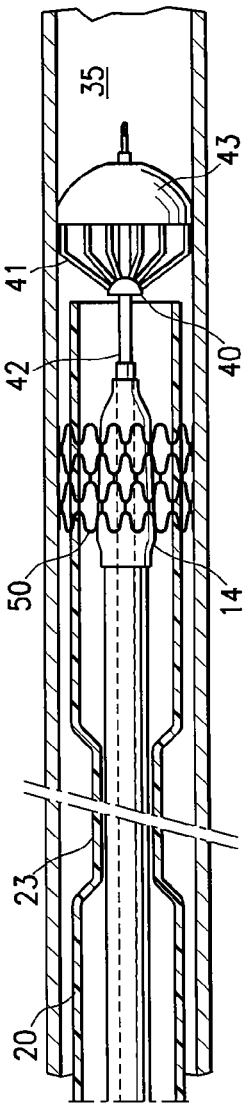

After being inflated, the balloon 14 is deflated and the recovery sheath 20 is unlocked and distally advanced over the deflated balloon within the expanded stent 50. Specifically, the operator holds the collar 34 stationary on the recovery sheath 20 while distally advancing the recovery sheath 20 over the stationary balloon catheter shaft 12 therein, to position the distal end of the recovery sheath 20 distal to the distal end of the balloon catheter 11 (i.e., distal to the distal end of the device lumen 15 at the distal tip of the catheter shaft 12). FIG. 10 illustrates the recovery sheath 20 advanced distally over the deflated balloon 14. Once within the recovery sheath 20, the balloon catheter 11 can be proximally withdrawn therein, typically to position the balloon at the proximal end of the distal recovery section 22 of the recovery sheath 20.

In accordance with the invention, the expanded embolic protection device frame 41 is then collapsed within the recovery sheath 20 by slidably displacing the sheath 20 relative to the embolic protection device 40. In a presently preferred embodiment, the recovery sheath 20 and balloon catheter 11 are advanced together distally, preferably locked together, to position the frame 41 within the recovery section 22 of the recovery sheath 20. The balloon deflates to a deflated configuration having wrinkles and folds or wings of excess balloon material forming a larger profile than the noninflated balloon, and as a result the deflated balloon preferably is maintained within the recovery sheath 20 to prevent the deflated balloon material from snagging on the stent or otherwise disadvantageously interacting with the stent 50 or vascular anatomy.

Figure 11:
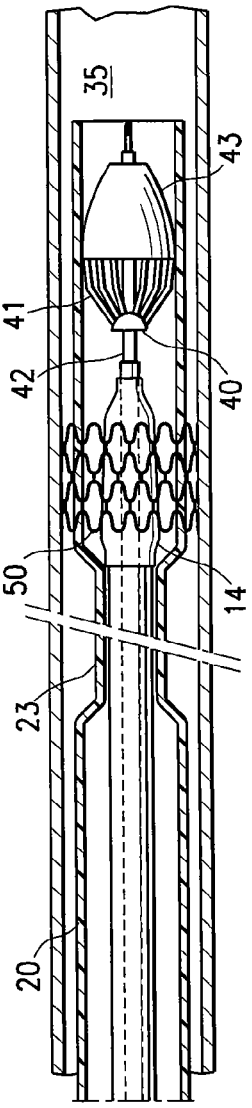

FIG. 11 illustrates the recovery sheath advanced, together with the balloon catheter 11 therein, to collapse the frame 41 in the distal recovery section 22 of the sheath 20. The inner surface of the distal recovery section 22 contacts a portion of the expanded frame 41 or a collapsing mechanism connected thereto such as control wires or other mechanisms as are conventionally known for embolic protection filters, thereby collapsing the frame 41 as the distal recovery section 22 is advanced distally. Following recovery of the device 40, the assembly of the balloon catheter system 10 with the collapsed frame 41 therein is slidably displaced in the patient's body lumen 35 to reposition or remove the frame 41 from the patient's body lumen 35.

The inner diameter of the distal recovery section 22 of the sheath 20 is configured to be sufficiently small to collapse the frame 41 by slidably advancing relative thereto, but also sufficiently large such that forcing the sheath 20 distally over the embolic protection device frame 41 does not break the connection between the frame 41 and the elongated core 42 of the embolic protection device 40. For example, in one embodiment, the embolic protection device 40 or other recoverable expandable device comprises an elongated body (i.e., core wire or shaft) having the expanded frame secured to a distal section thereof with a detach force of less than 1 pound, and the recovery section of the sheath 20 has an inner diameter configured to collapse the frame with a force which does not exceed the detach force of the frame.

The diameter of the recovery sheath 20 depends upon the size of the balloon 14 and expandable device 40 operative distal end. Typically the recovery sheath distal recovery section 22 has an inner diameter of about 0.048 to about 0.10 inches and an outer diameter of about 0.052 to about 0.12 inches, and the distal shaft section 23 has an inner diameter of about 0.02 to about 0.10 inches and an outer diameter of about 0.025 to about 0.12 inches, and the midshaft section 24 has an inner diameter of about 0.03 to about 0.12 inches and an outer diameter of about 0.04 to about 0.124 inches. The openwalled proximal shaft section 25 has a length of about 1 cm to about 110 cm, more specifically about 40 cm to about 110 cm. In an embodiment in which the proximal shaft section 25 has a tubular configuration, the inner diameter is about 0.025 to about 0.10 inches and the outer diameter is about 0.029 to about 0.12 inches.

Figure 13:
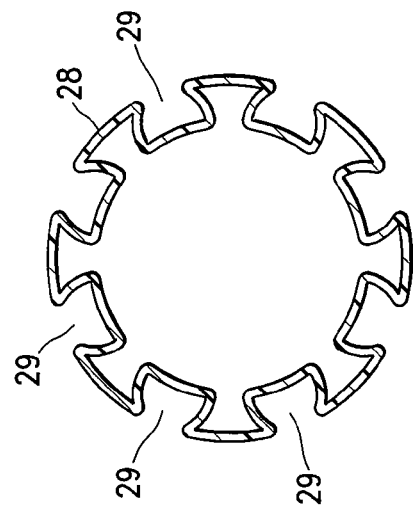
FIG. 13 is a transverse cross section of the recovery sheath of FIG. 12, taken along line 13-13.
Figure 15:
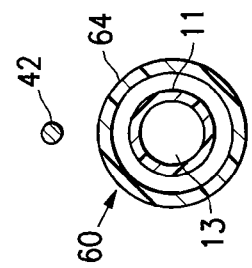
FIG. 15 is a transverse cross-section of the balloon catheter system of FIG. 14, taken along line 15-15.
Figure 12:
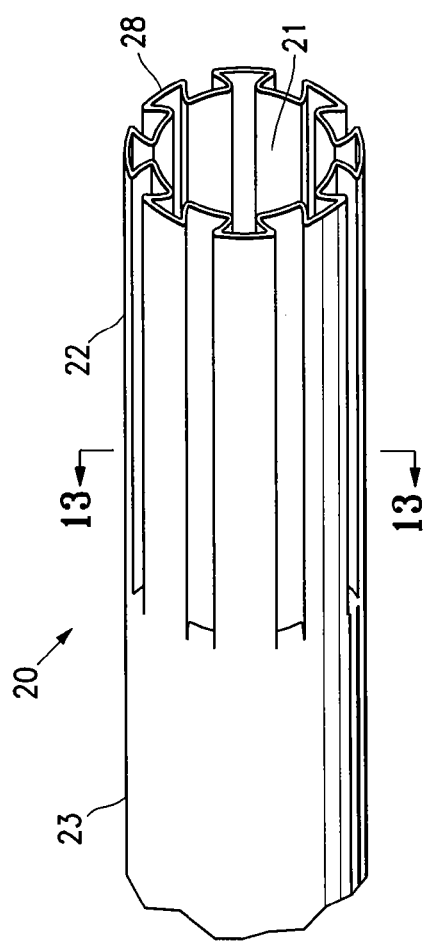
FIG. 12 is an perspective view of the distal end of an alternative recovery sheath embodying features of the invention, in which the recovery sheath has a corrugated distal recovery portion.

FIG. 12 illustrates an alternative embodiment of the invention, in which the recovery sheath 20 distal recovery section 22 has a corrugated wall 28 which unfolds from a radially collapsed configuration (illustrated) to a radially enlarged configuration (not shown). For ease of illustration the balloon catheter 11 is not shown in FIG. 12, although it should be understood that the recovery sheath 20 of FIG. 12 would be premounted on a balloon catheter 11 as in the embodiment of FIG. 1. The corrugated wall 28 has corrugation grooves which extend along at least a portion of the length of the distal recovery section 22. The corrugated wall 28 can have a variety of suitable folded configurations. However, as best shown in FIG. 13 illustrating a transverse cross section taken along line 13-13 in FIG. 12, in the illustrated embodiment, the corrugated wall 28 corrugation grooves are wider at a base of the groove than along a mouth 29 of the groove. As a result, unlike a wall merely folded with accordion pleats, a presently preferred embodiment of the corrugated wall 28 has folds which are designed to maximize the change in diameter produced thereby.

The corrugated wall 28 provides a low profile in the radially collapsed configuration which radially expands as needed during a method of the invention by causing the distal recovery section 22 to unfold to the radially expanded configuration upon application of a radially expansive force against an inner surface of the distal recovery section. Thus, as the recovery sheath corrugated distal recovery section 22 is advanced distally over the deflated balloon 14, the radially collapsed corrugated wall unfolds to increase the inner diameter of the recovery sheath along the distal recovery section 22 and facilitate advancement over the deflated balloon. In the fully radially enlarged configuration, the unfolded corrugated wall 28 has a uniform annular wall similar to that illustrated in FIG. 5. In a presently preferred embodiment, the corrugated wall 28 self-collapses to a radially re-collapsed configuration from the radially enlarged configuration upon the removal of the radially expansive force. Thus, as the recovery sheath corrugated distal recovery section 22 is advanced distally beyond the deflated balloon 14, the unfolded wall preferably re-folds to a radially re-collapsed configuration similar to that illustrated in FIG. 13. The re-collapsed configuration of the corrugated wall portion of the sheath 20 facilitates recovery of the expanded device 40. Specifically, the re-collapsed configuration of the corrugated wall has a diameter which is sufficiently small to collapse the frame and hold it in a low profile configuration for repositioning or removal from the body lumen. In one embodiment, the radially enlarged corrugated wall radially re-collapses to a low profile diameter which is about equal to the low profile diameter of the corrugated wall in the initial radially collapsed configuration (i.e., prior to being radially enlarged by advancement over the deflated balloon). Typically, the radially re-collapsed corrugated wall unfolds somewhat during recovery of the embolic protection filter frame 41, but to a diameter which is less than that of the radially enlarged configuration caused by advancement of the sheath over the deflated balloon.

Preferably, the corrugated wall portion is provided along the entire length of the distal recovery section 22 of the sheath 20, with the distal shaft section 23 of the sheath 20 (located proximally adjacent to the corrugated wall portion) having an annular uniform wall which is not corrugated or otherwise folded. The corrugated wall 28 is typically prepared by mechanically folding the tubular wall of the distal recovery section 22 compactly at an elevated temperature. Although discussed in term of the premounted, variable profile recovery sheath 20 of the illustrated embodiments, it should be understood that a variety of suitable recovery catheters can be provided with corrugated wall 28 along at least a distal end section thereof according to an embodiment of the invention, including a corrugated wall recovery catheter which is not premounted on a balloon catheter.

Figure 14:
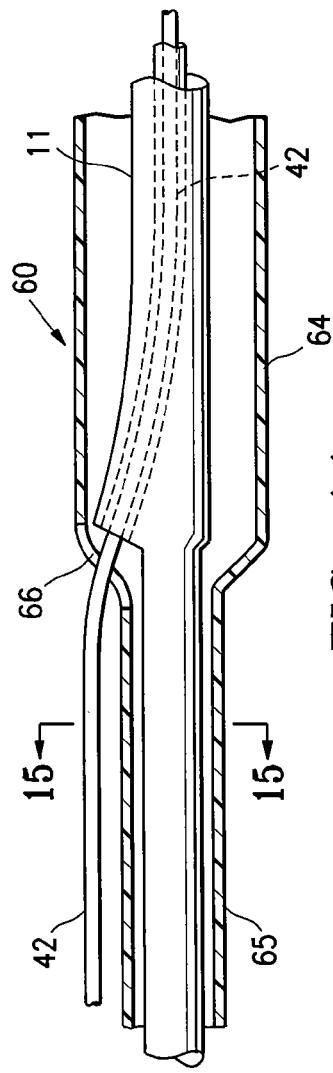
FIG. 14 illustrates an alternative embodiment of a balloon catheter system of the invention, in which the recovery sheath has a rapid exchange proximal port and a tubular proximal section extending fully around the balloon catheter shaft circumference.

FIG. 14 illustrates an alternative embodiment of a recovery sheath 60 having a proximal shaft section 65 which, unlike the open-walled proximal shaft section 25 of the recovery sheath 20 of FIG. 1, extends fully around the circumference of the balloon catheter 11 therein. FIG. 14 illustrates a portion of the sheath 60, located at the point at which the sheath proximal shaft section 65 transitions to the larger diameter midshaft section 64 distal thereto. In the embodiment of FIG. 14, the tubular body of the sheath 60 has a port 66 at the proximal end of the midshaft section 64 configured to slidably receive the proximal section (core wire 42) of the embolic protection device 40 therein to provide for rapid exchange.

In a presently preferred embodiment, the recovery sheath 20, 60 is formed of a single tubular member such that the distal recovery, distal shaft, midshaft, and proximal shaft sections 22, 23, 24, 25 of the sheath 20 are formed of the same polymeric composition, although an atraumatic soft distal tip may be provided at the distal end of the sheath 20. An atraumatic soft distal tip member is formed of a lower Shore durometer (softer) material than the section of the sheath 20 proximal thereto. The recovery sheath 20, 60 can be formed of a variety of suitable materials commonly used in catheter shaft construction including thermoplastic elastomers or thermoset plastics. For example, in one embodiment, the recovery sheath 20, 60 is formed at least in part of a cross-linked HDPE or other polyolefin, or a polyamide copolymer (a thermoplastic elastomer) such as a polyether block amide (PEBAX). Suitable materials have sufficient strength to hold the compressed strut assembly of the embolic protection device 40, and preferably provide a relatively lubricious, low friction surface to minimize friction between the filtering assembly and the distal recovery section 22 inner surface. The wall of the recovery sheath 20 can have a lubricity enhancing additive or coating. In one embodiment, a lubricious surface coating, such as a silicone lubricant, is provided on the inside surface of the recovery sheath 20 along at least the distal recovery section 22 to further reduce the frictional force during contact with the embolic protection device 40.

The length of the various sections of the recovery sheath 20, 60 will depend on a variety of factors including the size of the balloon catheter shaft 12 and balloon 14. The total length of the recovery sheath 20, 60 is generally about 45 to about 125 cm, and is typically about 30 to about 90% of the total length of the balloon catheter 11. The length of the distal recovery section 22 of the sheath varies from about 25 to about 110 mm depending on the balloon 14 size and the type of expandable device 40 to be recovered therein, and more specifically in one embodiment ranges from about 5 to about 10% of the total length of the sheath. Depending on the size of the balloon catheter 11, the distal recovery section 22 of the sheath may be longer or shorter than the length of the distal shaft section 23 of the sheath 20. The sheath midshaft section 24 is typically about 1 cm longer than the distal recovery section 22 of the sheath, to ensure that the sheath 20 can be fully advanced or retracted over the balloon catheter rapid exchange notch as required.

The dimensions of balloon catheter 11 are determined largely by the size of the balloon and guidewire to be employed, the catheter type, and the size of the artery or other body lumen through which the catheter must pass or the size of the stent. The overall length of the catheter 11 may range from about 100 to about 150 cm, and is typically about 143 cm. Typically, the outer tubular member 19 has an outer diameter of about 0.02 to about 0.04 inch (0.05 to 0.10 cm), and the wall thickness of the outer tubular member 19 can vary from about 0.002 to about 0.008 inch (0.0051 to 0.02 cm), typically about 0.003 to 0.005 inch (0.0076 to 0.013 cm). The inner tubular member 18 typically has an inner diameter of about 0.01 to about 0.018 inch (0.025 to 0.046 cm), and a wall thickness of about 0.004 to about 0.008 inch (0.01 to 0.02 cm). Preferably, balloon 14 has a length about 0.8 cm to about 6 cm, and an inflated working diameter of about 2 mm to about 10 mm.

The various catheter 10 components may be joined using conventional bonding methods such as by fusion bonding or use of adhesives. Although the shaft 12 is illustrated as having an inner and outer tubular member 18, 19, a variety of suitable shaft configurations may be used including a dual lumen extruded shaft having a side-by-side lumens extruded therein.

While the present invention is described herein in terms of certain preferred embodiments, those skilled in the art will recognize that various modifications and improvements may be made to the invention without departing from the scope thereof. For example, although discussed primarily in terms of recovery of an embolic protection filter having a frame of spaced apart, longitudinal struts, alternative reversibly expandable devices can be recovered using a catheter system of the invention, including embolic protection devices not having this frame-type construction, and expanded agent/drug delivery devices, and the like. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments of the invention.

What is claimed:

1. A balloon catheter system configured to recover an expanded device in a patient's body lumen, comprising:

a) a balloon catheter having a proximal end, a distal end, an elongated shaft with an inflation lumen and a device lumen therein, and a balloon on a distal shaft section with an interior in fluid communication with the inflation lumen; and b) a recovery sheath having a wall and a single lumen with the balloon catheter elongated shaft slidably disposed therein, and having a proximal end, a distal end, a retracted configuration in which the distal end is located proximal to the balloon, and an advanced configuration in which the distal end is located distal to the balloon catheter, and having a transverse cross sectional profile which decreases from a large profile distal recovery section to smaller profile distal shaft section, and which increases from the distal shaft section to a larger profile midshaft section, and which decreases from the midshaft section to a smaller profile proximal shaft section, the recovery sheath including a longitudinally extending opening that is cut into the wall of the proximal shaft section to form a channel having a substantial C-shape that extends along at least a portion of the proximal shaft section.

2. The balloon catheter system of claim 1 wherein the sheath has a tubular body extending from the proximal to the distal end of the sheath with the sheath lumen extending therein, and the sheath lumen has a diameter which decreases from the distal recovery section to the distal shaft section, and increases from the distal shaft section to the midshaft section, and decreases from the midshaft to the proximal shaft section.

3. The balloon catheter system of claim 1 wherein the sheath has a tubular body portion extending from the midshaft section to the distal end of the sheath with the sheath lumen extending therein such that the sheath extends fully around the circumference of the elongated shaft along the mid, distal and recovery sections, and the channel formed on the proximal shaft section of the sheath is configured to extend only partially around the circumference of the elongated shaft of the balloon catheter therein.

4. The balloon catheter system of claim 3 wherein the sheath lumen has a diameter which decreases from the distal recovery section to the distal shaft section and which increases from the distal shaft section to the midshaft section.

5. The balloon catheter system of claim 1 wherein the balloon catheter is a rapid exchange catheter having a proximal shaft section and a distal shaft section with the device lumen extending in the distal shaft section to a proximal port spaced distally from the proximal end of the elongated catheter shaft, and the sheath midshaft section extends across the device lumen proximal port in the retracted and advanced configurations.

6. The balloon catheter system of claim 1 wherein the sheath distal recovery, distal shaft, midshaft, and proximal shaft sections are formed of the same polymeric composition.

7. The balloon catheter system of claim 6 including an atraumatic soft tip secured to the distal end of the sheath distal recovery section, which defines a distal tip section of the sheath lumen, and which is formed of a lower Shore durometer hardness polymeric material than a portion of the sheath proximal thereto.

8. The balloon catheter system of claim 1 wherein the proximal end of the sheath is located distal to the proximal end of the balloon catheter elongated shaft in the retracted configuration.

9. The balloon catheter system of claim 1 wherein the distal recovery section of the sheath has at least a portion with a corrugated wall which unfolds from a radially collapsed configuration to a radially enlarged configuration.

10. The balloon catheter system of claim 9 wherein the corrugated wall of the distal recovery section unfolds to the radially enlarged configuration upon application of a radially expansive force against an inner surface thereof, and the corrugated wall self-collapses to a radially re-collapsed configuration from the radially enlarged configuration upon the removal of the radially expansive force.

11. The balloon catheter system of claim 1 wherein the longitudinally extending opening on the proximal shaft section extends along the entire length of the proximal shaft section of the recovery sheath.

12. The balloon catheter system of claim 1 wherein the longitudinally extending opening extends partially into the mid shaft section of the recovery sheath.

13. The balloon catheter system of claim 12 wherein the longitudinally extending opening on the proximal shaft section extends along the entire length of the proximal shaft section of the recovery sheath.

14. A balloon catheter system configured to recover an expanded device in a patient's body lumen, comprising:
a) a balloon catheter having a proximal end, a distal end, an elongated shaft with an inflation lumen and a device lumen therein, and a balloon on a distal shaft section with an interior in fluid communication with the inflation lumen; and
b) a recovery sheath having a single lumen with the balloon catheter elongated shaft slidably disposed therein, and having a proximal end, a distal end, a retracted configuration in which the distal end is located proximal to the balloon, and an advanced configuration in which the distal end is located distal to the balloon catheter, and having a transverse cross sectional profile which decreases from a large profile distal recovery section to smaller profile distal shaft section, and which increases from the distal shaft section to a larger profile midshaft section, and which decreases from the midshaft section to a smaller profile proximal shaft section, the sheath lumen extending from a distal port in the distal end of the sheath to a proximal port at a location at which the recovery sheath transitions from a tubular shape to an open-walled proximal section with a C-shaped inner surface which defines a channel and which is configured to extend only partially around the circumference of the balloon catheter elongated shaft.

15. The balloon catheter system of claim 14 wherein the sheath has a tubular shape along the distal recovery section, the distal shaft section and the midshaft section.

16. The balloon catheter system of claim 15 wherein the open-walled proximal section extends from the proximal end of the recovery sheath to the tubular midshaft section.

17. The balloon catheter system of claim 14 including a releasable lock mechanism configured to releasably lock the recovery sheath to the balloon catheter shaft.

18. The balloon catheter system of claim 14 wherein the open-walled proximal section of the sheath has a longitudinally extending opening in the wall which is wider than the section of the balloon catheter shaft extending in the channel defined by the open-walled proximal section, and including a collar disposed on the sheath which holds the balloon catheter shaft within the sheath channel and which constrains the sheath rotational orientation relative to the balloon catheter shaft.

19. The balloon catheter system of claim 14 wherein the balloon catheter is a rapid exchange catheter having a proximal shaft section and a distal shaft section with the device lumen extending in the distal shaft section to a proximal port spaced distally from the proximal end of the balloon catheter shaft, and the open-walled proximal section of the sheath has a length sufficiently long to extend along substantially the entire length of the proximal shaft section of the balloon catheter.

20. The balloon catheter system of claim 14 wherein the open-walled proximal shaft section of the sheath extends along the entire length of the proximal shaft section of the recovery sheath.

21. The balloon catheter system of claim 14 wherein the open-walled proximal shaft section extends partially into the mid shaft section of the recovery sheath.

22. The balloon catheter system of claim 14 wherein the open-walled proximal shaft section of the sheath extends partially along the length of the proximal shaft section.

* * * * *